(12) United States Patent
Chinnapillai et al.

(10) Patent No.: US 7,872,132 B2
(45) Date of Patent: Jan. 18, 2011

(54) INTERMEDIATES USEFUL FOR THE PREPARATION OF ARIPIPRAZOLE AND METHODS FOR THE PREPARATION OF THE NOVEL INTERMEDIATES AND ARIPIPRAZOLE

(75) Inventors: Rajendiran Chinnapillai, Hyderabad (IN); Veera Reddy Arava, Hyderabad (IN); Venkata Subba Rao Athukuru, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 956 days.

(21) Appl. No.: 11/664,849

(22) PCT Filed: Oct. 8, 2004

(86) PCT No.: PCT/IN2004/000316

§ 371 (c)(1),
(2), (4) Date: Apr. 6, 2007

(87) PCT Pub. No.: WO2006/038220

PCT Pub. Date: Apr. 13, 2006

(65) Prior Publication Data

US 2009/0203907 A1      Aug. 13, 2009

(51) Int. Cl.
*C07D 401/12* (2006.01)
(52) U.S. Cl. .................................................. 544/363
(58) Field of Classification Search .................. 544/363
See application file for complete search history.

(56) References Cited

U.S. PATENT DOCUMENTS 5,006,528 A    4/1991    Oshiro et al.
6,995,264 B2   2/2006    Tsujimori et al.
2004/0058935 A1  3/2004  Bando et al.
2007/0202181 A1  8/2007  Bando et al.
2008/0299216 A1* 12/2008 Czarnik ...................... 424/600

FOREIGN PATENT DOCUMENTS

EP     0 043 971 A1    1/1982
GB        850663       10/1960
WO   WO 2003/026659    4/2003

OTHER PUBLICATIONS

Tomita, M. et al., "The Schmidt Reaction with Benzocycloalkenones", J. Chem.Soc.(C) 1969, pp. 183-188.
O. Friedman et al., "Synthesis of Cyclized Derivatives of New Secondary Nitrogen Mustards RElationship of Structure to Toxicity," J. Am. Chem.Soc., 1960, 82, p. 5202.
Oshira, Y., "Novel Antipsychotic Agents with Dopamine Autoreceptor Agonist Properties: Synthesis . . . ", J. Med. Chem. 1998, 41, pp. 658-667.

* cited by examiner

*Primary Examiner*—James O Wilson
*Assistant Examiner*—Ebenezer Sackey
(74) *Attorney, Agent, or Firm*—IpHorgan Ltd.

(57) ABSTRACT

An improved process for the preparation of aripiprazole (1) which comprises (i) reacting 6-hydroxy-l-indanone (11) with 1,4-dihalobutane (12) in the presence of a base and a solvent at a temperature in the range of 90 to 110 deg C to form the novel intermediate 6-(4-halo butoxy)-indan-1-one (3), (ii) reacting the novel intermediate with 1-(2,3-clichlorophenyl)-piperazine (9) to get another novel intermediate 6-[4-[4-(2,3-dichlorophenyl)-l-piperazinyl]butoxy]-indan-l-one (2) and (iii) reacting the resulting novel compound with sodium azide. The invention also relates to the novel intermediates of the formulae (2) & (3) and processes for their preparation. The invention also includes intermediate compounds useful for the preparation of aripiprazole.

13 Claims, No Drawings

INTERMEDIATES USEFUL FOR THE PREPARATION OF ARIPIPRAZOLE AND METHODS FOR THE PREPARATION OF THE NOVEL INTERMEDIATES AND ARIPIPRAZOLE

INTRODUCTION

The present invention relates to a novel intermediates useful for the preparation of Aripiprazole and methods for the preparation of the novel intermediates and Aripiprazole. Aripiprazole, which is, 7-[4-[4-(2,3-dichlorophenyl)-1-piperazinyl]-butoxy]-3,4-dihydrocarbostyril has the formula (1) as given below

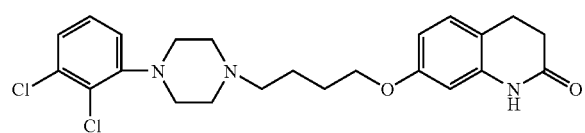

1

The invention also relates to a novel intermediate of the formulae (2) and (3) which is useful for the preparation of Aripiprazole of the formula (1). The present invention also relates to a process for the preparation of the said novel intermediate of the formula (2). The present invention also relates to an improved process for the preparation of Aripiprazole of the formula (1) using the novel intermediate of the formula (2).

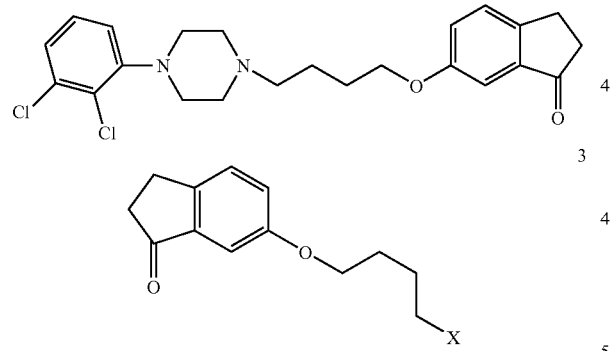

2

3

Aripiprazole 7-[4-[4-(2,3-dichlorophenyl)-1-piperazinyl]-butoxy]-3,4-dihydrocarbostyril or 7-[4-[4-(2,3-dichlorophenyl)-1-piperazinyl]-butoxy]-3,4-(2H)-quinolinone is commercially marketed pharmaceutically active substance for atypical antipsychotic drug useful for the treatment of schizophrenia. The usefulness of the Aripiprazole as a typical antipsychotic agents is mentioned in J. Med. Chem., (1998), 4, 658-667.

The process for the preparation and the properties of the antipsychotic drug aripiprazole, 7-[4-[4-(2,3-dichlorophenyl)-1-piperazinyl]-butoxy]-3,4-dihydrocarbostyril of the formula (1) have been described in U.S. Pat. No. 5,006,528 which corresponds to EP No 367141 and launched in the US in November 2002 by Bristol-Mayer Squibb/Otsuka for the treatment of schizophrenia.

Hitherto it has been found that the U.S. Pat. No. 5,006,528 describes the process for the preparation of the Aripiprazole using five different routes as described in the scheme-1

Scheme-1

Route-1

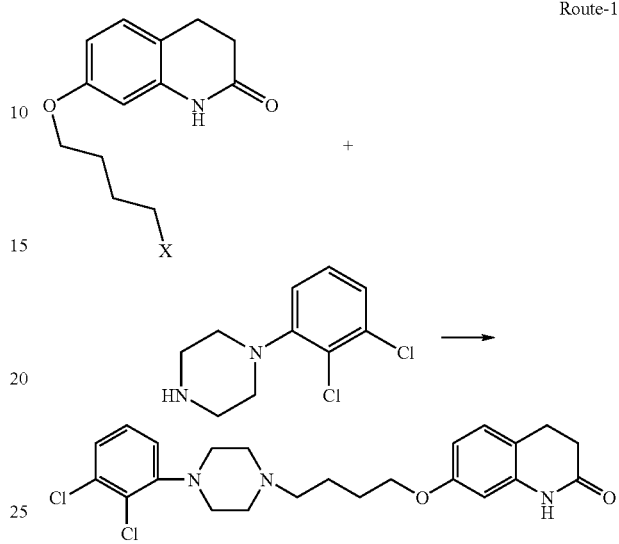

Route-2

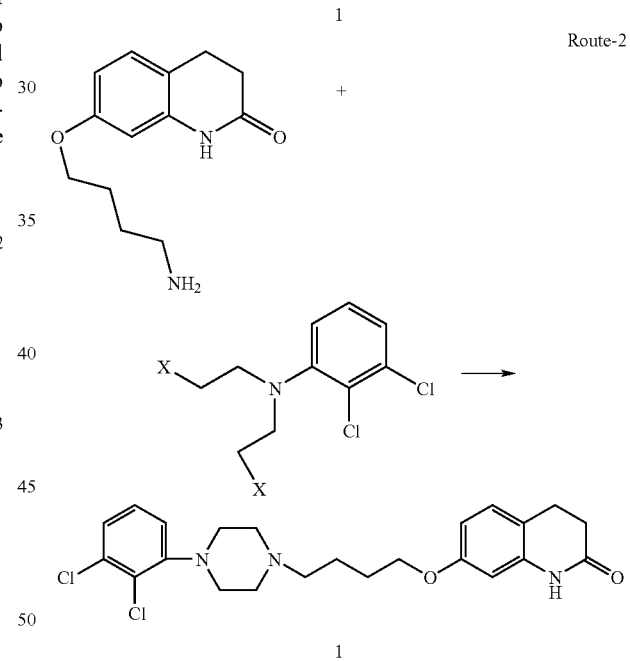

Route-3

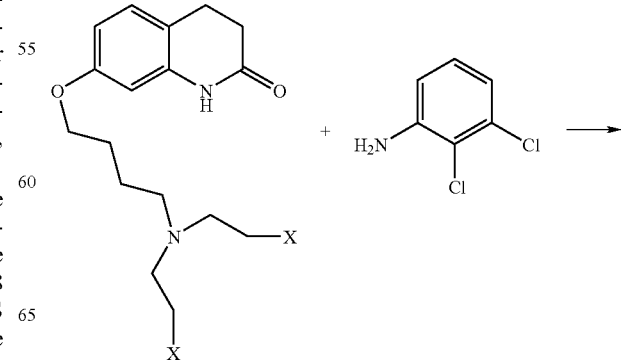

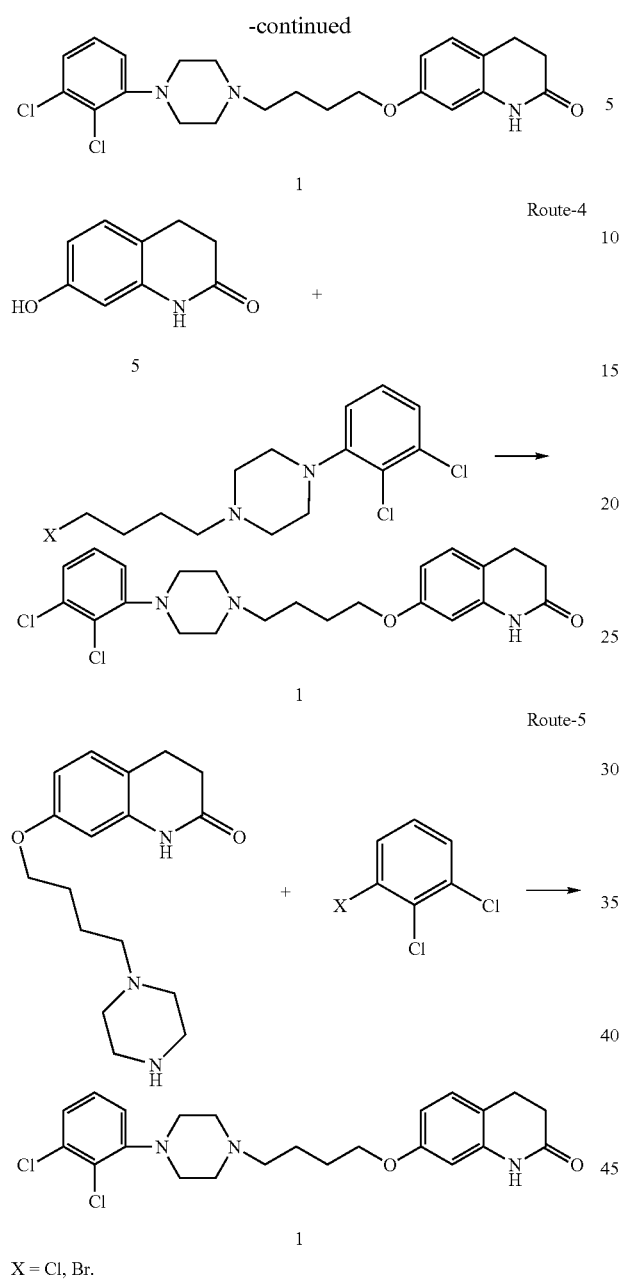

X = Cl, Br.

Further in WO Pat No 2003026659 discloses the process for the preparation of low hygroscopic Aripiprazole and in WO Pat No 20040663162 discloses the process for the preparation of aripiprazole in high purity using the same route as mentioned in the route-1 (scheme-1) by conducting the reaction in water medium.

All the above mentioned methods revolve around the same type of intermediates indicated above. The main intermediate 7-hydroxy-2,3-dihydrocarbostyril of the formula (5) is prepared from 3-hydroxy aniline of the formula (6) and 3-chloropropionylchloride of the formula (7) as depicted in scheme-2.

In this method besides the required product of the formula (5) the other unwanted isomer of the formula (8) also forms, which is very difficult to remove and this impurity is continue to be present in the final drug aripiprazole and during the removal process the yield becomes very low.

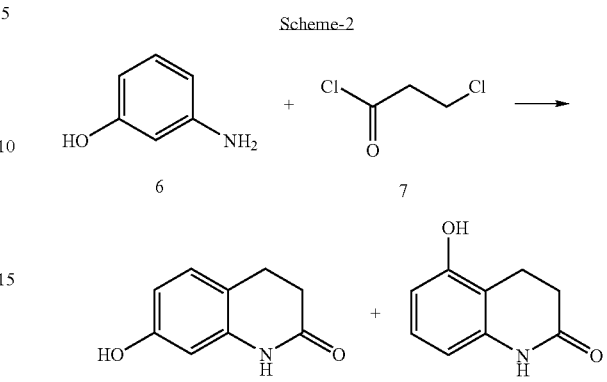

This has prompted and necessitated further research in an attempt to develop a novel route to avoid the formation of the impurity and to maximize the yield. Further given the increasing therapeutic value of aripiprazole, the applicant set itself the objective and undertook research studies with the aim of developing a new synthetic route to prepare 7-{4-[4-(2,3-dichlorophenyl)-1-piperazinyl]-butoxy}-3,4-dihydrocarbostyril which would make it possible to obtain this compound in a sufficient purity and economically acceptable yield.

Therefore the main objective of the present invention is to provide an improved method for the preparation of aripiprazole avoiding the drawbacks of the hitherto known processes.

Yet another objective of the present invention is to provide novel intermediates of the formulae (2) & (3) useful for the preparation of aripiprazole Still another objective of the present invention is to provide processes for the preparation of novel intermediates of the formulae (2) & (3) useful for the preparation of aripiprazole.

This process of the present invention is illustrated in the scheme-3 shown below

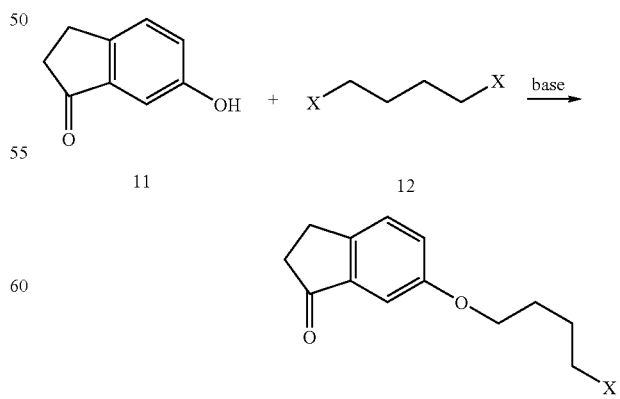

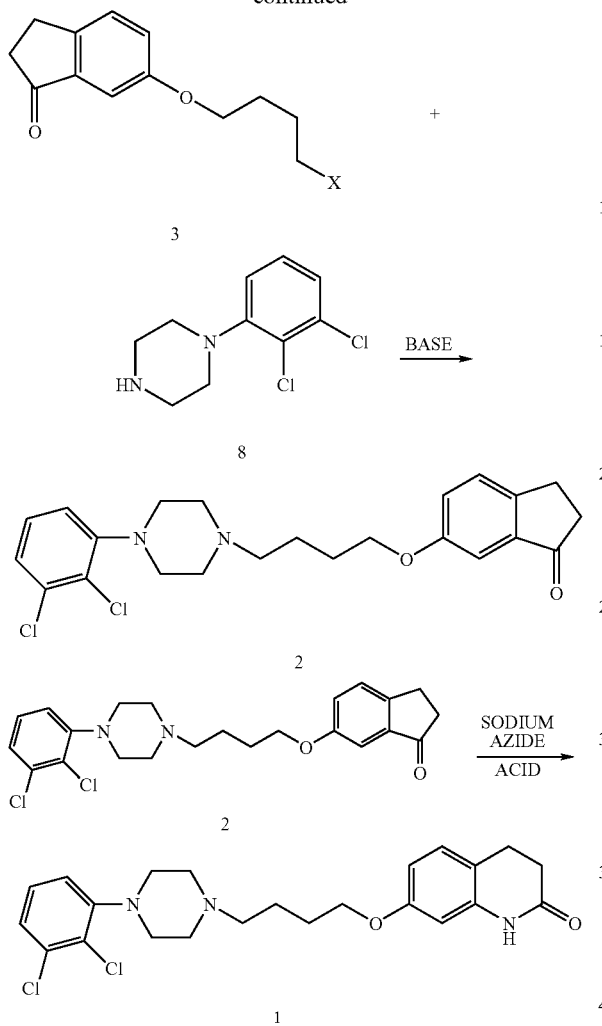

Accordingly, the present invention provides novel intermediates 6-[4-[4-(2,3-dichlorophenyl)-piperazin-1-yl]-butoxy]-indan-1-one of the formula (2) & 6-(4-halobutoxy)-indan-1-one of the formula (3) which are useful for the preparation of aripiprazole of the formula (1).

According to another embodiment of the present invention there is provided processes for the preparation of novel intermediates 6-[4-[4-(2,3-dichlorophenyl)-piperazin-1-yl]butoxy]-indan-1-one of the formula (2) & 6-(4-halobutoxy)-indan-1-one of the formula (3) which are useful for the preparation of aripiprazole of the formula (1).

Accordingly the present invention provides a process for the preparation of novel intermediate of the formula (3) useful for the preparation of aripiprazole of the formula (1) which comprises reacting the compound of the formula (11)

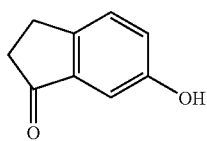

with 1,4-dihalobutane of the formula (12)

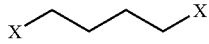

wherein, X represents Cl or Br in the presence of a base and a solvent at a temperature in the range of 90 to 110 deg C. to form the novel intermediate of the formula (3).

According to another embodiment of the present invention there is also provided a process for the preparation of another novel intermediate of the formula (2) useful for the preparation of aripiprazole of the formula (1) which comprises (i) Reacting the compound of the formula (11) with 1,4-dihalobutane of the formula (12) where, X represents Cl or Br in the presence of a base and a solvent at a temperature in the range of 90 to 110 deg C. to form the novel intermediate of the formula (3) and (ii) Reacting the novel compound of the formula (3) obtained in step (i) with 1-(2,3-dichlorophenyl)-piperazine of the formula (9)

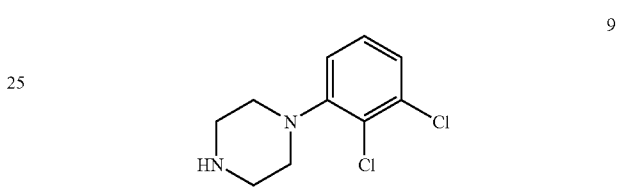

in the presence of a base and a phase transfer catalyst and a solvent at a temperature in the range of 80 to 120 degree C. to form the novel intermediate of the formula (2).

According to yet another embodiment of the present invention there is provided an improved process for the preparation of aripiprazole of the formula (1) which comprises (i) Reacting the compound of the formula (11) with 1,4-dihalobutane of the formula (12) where, X represents Cl or Br in the presence of a base and a solvent at a temperature in the range of 90 to 110 deg C. to form the novel intermediate of the formula (3), (ii) Reacting the novel compound of the formula (3) obtained in step (i) with the compound of the formula (9) in the presence of a base and a phase transfer catalyst and a solvent at a temperature in the range of 80 to 120 degree C. to form the novel intermediate of the formula 2 and (iii) Reacting the resulting novel compound of the formula (2) with sodium azide or trimethylsilylazide in the presence of a acids (Schmidt reaction) at a temperature between 50 to 90 degree C. to obtain the compound of the formula (1).

The base such as sodium hydride, sodium methoxide, triethylamine, potassium carbonate, sodiumbicarbonate and sodium carbonate preferably triethylamine most preferably potassium carbonate may be used in step (i). The solvents used may be selected from acetone, chloroform, methylene chloride, ethylene dichloride, dimethyl formamide, dimethylsulphoxide, acetonitrile and the like. preferable solvent being acetone and most preferable 1,4-dihalobutane itself as a solvent. The 1,4-dihalobutane can be used 1-6 equivalent with respect to 6-hydroxyindan-1-one. The preferred mole equivalent is 4-6 equivalent. The reaction temperature may preferably between 90-110° C. and most preferably between 100-110° C.

The phase transfer catalyst used for the step-(i) are tetrabutylammonium chloride, tetrabutylammoniumbromide, benzyltriethylammonium chloride, phenyltrimethylammonium chloride.

The base used in step (ii) includes sodium carbonate, potassium carbonate, sodium bicarbonate, potassium bicarbonate, sodium hydride, potassium hydride and triethylamine, most preferably sodium carbonate. The solvents used for the reaction in step (ii) may be selected from acetonitrile, acetone, dimethyl formamide, dimethyl sulfoxide, ethanol, methanol, n-Butanol and water, preferable solvent is acetone and water and most preferable is water. The temperature for the reaction in step (ii) may be between 80-120° C. and most preferably between 100-120° C. The phase transfer catalyst used is tetra butylammonium chloride, tetra butylammonium bromide, benzyl triethyl ammonium chloride, phenyltrimethyl ammonium chloride.

The acids used in step (iii) includes sulfuric acid, aluminum chloride, boron trifluoro etherate, trifluoro acetic acid, methane sulfonic acid, chloroacetic acid, dichloroacetic acid, trichloroacetic acid and trifluoro methane sulfonic acid. The preferred acids are trifluoro acetic acid and methane sulfonic acid, most preferred acid is trifluoro acetic acid. The temperature of the reaction may be between 50-90° C. and most preferably between 50-70° C. The azides used in the reaction are sodium azide and trimethylsilylazide, most preferred is sodium azide. The amount of sodium azide may be 1-5 moles preferably between 1.5-4 moles equivalent with respect to the compound of the formula (2) used. The crystallization may be done using acetone, methanol, toluene, ethyl acetate, methylene chloride, dimethylformamide, dimethyl sulfoxide and the mixture thereof. The preferred solvent is acetone and the most preferred solvent is methanol.

The compound 1-(2,3-dichlorophenyl)-piperazine of formula (9) can be prepared according to techniques commonly known in the art disclosed in GB 850663 and 6-hydroxyindan-1-one of the formula (11) may be obtained by the method described in J. Am. Chem. Soc., (1960), 21, 5202.

The present invention is more particularly described and explained in the following Examples. It is to be understood, however, that the present invention is not limited to these examples, which are given only to illustrate the invention. Therefore various changes and modifications may be made without departing from the scope of the present invention. In these examples the melting points were determined by PERKIN ELMER-PYRIS, IR Spectra were recorded in FTIR PERKIN ELMER Instrument, Differential scanning calorimetry (DSC) with temperature gradient of 20° C./Min. The mass spectra were recorded with LC-MS/API 4000. The Nuclear magnetic resonance (NMR) spectra were recorded with BRUKER 400 Hz in TMS as internal standard. The chemical shift are indicated in δ (ppm). The letters indicated s, d, dd, t, q and m respectively indicates a Singlet, a doublet, a doublet of doublet, a triplet, a quartet and multiplet.

EXAMPLE-I

Step-1

Process for the Preparation of the New Intermediate 6-(4-chloro butoxy)-indan-1-one of the Formula (3)

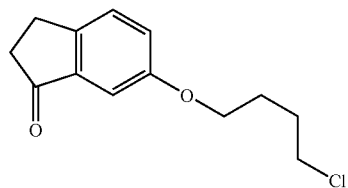

3

Mixture of 6-hydroxyindan-1-one of the formula (11) (20 gm, 0.135 mol), potassium carbonate (40 gm, 0.289 mol), 1,4-dichlorobutane (80 ml, 0.73 mol) and tetrabutyl ammonium bromide (2 g) was stirred for 1-3 hrs at 95° C. then distilled off excess 1,4-dichloro butane, diluted with water (80 ml). The aqueous layer was extracted with ethyl acetate, and the extract was washed with water, dried and evaporated off under reduced pressure to dryness. The evaporation residue is purified by crystallization using isopropyl ether as a solvent gave 29.5 gm of novel 6-(4-CHLORO BUTOXY)-INDAN-1-ONE of the formula (3).

MR=58.19° C.,

IR (cm$^{-1}$): 1697.88, 1616.31, 1492.71, 1296.57, 1055.33, 837.51, 720.75.

PMR: δ: 1.96 (m, 4H), 2.70 (m, 2H), 3.06 (t, 2H), 3.61 (t, 2H), 4.02 (t, 2H), 7.18 (m, 2H), 7.36 (d, 1H).

CMR: δ: 24.99 (t), 26.45 (t), 29.19 (t), 36.87 (t), 44.54 (t), 67.31 (t), 105.56 (d), 124.12 (d), 127.30 (d), 138.11 (s), 147.84 (s), 158.49 (s) 206.75 (s).

Mass spectrum: m/z (%)=[M+1] 239 (100), 197.1 (15.7), 161.2 (48.8), 149.0 (22.8), 107.1 (27.8).

Step-2

Process for the Preparation of Novel 6-[4-[4-(2,3-dichlorophenyl)-1-piperazinyl]butoxy]-indan-1-one of the Formula (2)

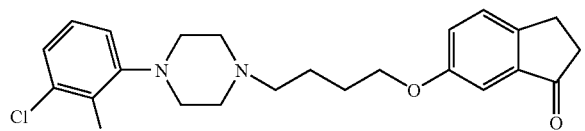

2

The 6-(4-CHLORO BUTOXY)-INDAN-1-ONE of the formula (3) obtained by the process described in step (1) (20 gm, 0.0838 mol), sodium carbonate (40 gm, 0.377 mol), tetrabutyl ammonium bromide (4 gm) and 1-(2,3-dichlorophenyl)-piperazine hydrobromide (28 gm, 0.0897) in water were stirred for 4-6 hrs at 95° C. After the completion of reaction the precipitated product was filtered and washed with water to get we product which on treatment with chloroform and Hydrochloric acid gave 30 g of 6-[4-[4-(2,3-dichlorophenyl)-1-piperazinyl]butoxy]-indan-1-one hydrochloride. This on basification with aqueous ammonia and extraction with chloroform followed by distillation gave novel 6-[4-[4-(2,3-dichlorophenyl)-1-piperazinyl]butoxy]-indan-1-one of the formula (2) 22 gm.

MR: 95.39° C., IR (cm$^{-1}$): 1711.81, 1576.39, 1474.07, 1448.34, 1292.80, 1274.96, 1240.72, 994.75, 963.85, 775.15, 712.75, MR: δ: 1.72 (m, 2H), 1.84 (m, 2H), 2.48 (t, 2H), 2.65 (m, 2H), 2.71 (t, 2H) 3.06 (m, 2H), 4.02 (t, 2H), 6.95 (q, 2H), 7.14-7.37 (m, 5H). CMR: δ: 23.16 (t), 24.86 (t), 26.89 (t), 36.74 (t), 51.09 (t), 53.05 (t), 57.88 (t), 67.82 (t), 105.32 (d), 118.36 (t), 124.06 (d), 124.21 (d), 127.11 (d), 127.22 (d), 133.69 (s), 137.93 (s), 147.54 (s), 151.07 (s), 158.49 (s), 206.62 (s), Mass spectrum: m/z (%): [m+1]=433.5 (36.7), 285.3 (20.5), 161.6 (100).

Step 3

Process for the Preparation of 7-[4-[4-(2,3-dichlorophenyl)-1-piperazinyl]butoxy]-3,4 dihydro-1(H)-quinoline-2-one(aripiprazole) of the Formula 1

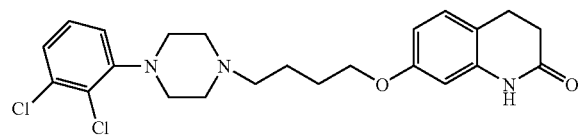

The 6-[4-[4-(2,3-dichlorophenyl)-1-piperazinyl]butoxy]-indan-1-one prepared by the step ((15 gm, 34.63 mmol) and 90 ml of trifluoroacetic acid was added and sodium azide (9 gm, 138.46 mmol) was added in portion wise at 65° C. The reaction mixture was maintained at 65° C. for 8-10 hrs. After the maintenance period was over the reaction mixture was quenched into 100 gm crushed ice, extracted with chloroform, and the chloroform basified with aqueous ammonia solution and separated the organic layer. The organic layer was dried with anhydrous sodium sulphate and concentrated under reduced pressure to get a residue 19 g. Which on crystallisation with methanol/toluene and acetone to give pure Aripiprazole of the formula 1.

MR: 136.02° C.:

IR (cm$^{-1}$): 1677.95, 1626.97, 1595.06, 1521.51, 1447.24, 1376.84, 1172.27, 960.70, 778.54.

PMR: δ: 1.69 (m, 2H), 1.81 (m, 2H), 2.48 (t, 2H), 2.62 (m, 6H), 2.89 (t, 2H), 3.07 (m, 4H), 3.95 (t, 2H), 6.31 (d, 1H), 6.53 (dd, 1H), 6.96 (q, 1H), 7.02 (d, 1H), 7.14 (m 2H,), 8.00 (s, 1H).

CMR: δ: 23.34 (t), 24.49 (t), 27.20 (t). 31.00 (t), 51.26 (t), 53.20 (t), 58.10 (t), 67.81 (t), 102.25 (d), 108.68 (d), 115.55 (s), 118.50 (d), 124.41 (d), 127.34 (d), 127.40 (d), 128.45 (d), 133.91 (s), 138.21 (s), 151.25 (s), 158.62 (s), 172.31 (s).

Mass spectrum: m/z(%): [M+1]=448.2 (100), 285.5 (74.2), 218.5 (22.8), 176.5 (20.0).

EXAMPLE 2

Step 1

Process for the Preparation of 6-(4-bromo butoxy)-indan-1-one of the Formula (3)

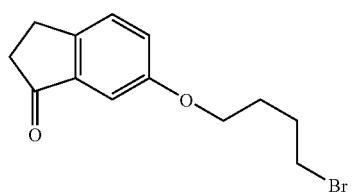

A mixture of 6-hydroxyindan-1-one (100 gm, 0.675 mol), potassium carbonate (96 gm, 0.695 mol), 1,4-dibromo butane (365 gm, 1.69 mol) and tetrabutyl ammonium bromide in acetone was introduced in to a three necked round bottomed flask filtered with a water condenser and a mechanical stirrer. The mixture was brought to a temperature 65° C. and maintained at 65° C. for nine hours and then distilled off solvent, diluted with water (400 ml). The aqueous layer was extracted with ethyl acetate, and the extract was washed with water, dried and evaporated in the rotavapour under reduced pressure to get a residue which on crystallization from isopropyl ether gave 125 gm of 6-(4-bromo butoxy)-indan-1-one of the formula 3

MR: 60.59° C.

IR: (cm$^{-1}$): 1705.61, 1610.51, 1488.19, 1294.21, 1021.54, 836.60, 558.98.

PMR: δ: 1.94 (m, 2H), 2.06 (m, 2H), 2.71 (m 2H), 3.06 (t, 2H), 3.47 (t, 2H) 4.01 (t, 2H), 7.17 (m, 2H), 7.36 (d, 1H).

CMR: δ : 25.01 (t), 27.69 (t), 29.35 (t), 33.18 (t), 36.01 (t), 67.19 (t), 105.57 (d), 124.16 (d), 127.31 (d), 138.13 (s), 147.87 (s), 158.50 (s) 206.77 (s). Mass spectrum: m/z (%)= [M+1] 283.4 (55.1), 161.1 (66.1), 149.4 (40.4), 135.4 (100), 106.9 (38.2),

Step-2

Process for the Preparation of 6-[4-[4-(2,3-dichlorophenyl)-1-piperazinyl]butoxy]-indan-1-one A mixture of 6-(4-bromobutoxy)-indan-1-one prepared by the process described in step (1) above (100 gm, 0.282 mol, 80% purity) and sodium iodide (42 gm, 0.28 mol) in acetonitrile was refluxed for 30 minutes and then cooled to room temperature. 1-(2,3-dichlorophenyl)-piperazine hydrochloride (68 gm, 0.294 mol) and triethyl amine (77 gm, 0.761 mol) were added to the mixture and the resulting mixture was refluxed for 4-6 hr. After solvent was removed, the residue thus obtained was dissolved in chloroform, washed with water which treatment with chloroform and Hydrochloric acid gave 140 g of 6-[4-[4-(2,3-dichlorophenyl)-1-piperazinyl]butoxy]-indan-1-one hydrochloride. This on chloroform solution was basified with ammonium hydroxide to pH 9.5 and extracted with chloroform twice 2×500 ml. The combined chloroform layer was concentrated using rotavapour under reduced pressure to get a residue which on purification with methanol gave 85 gm of 6-[4-[4-(2,3-dichlorophenyl)-1-piperazinyl]-butoxy]-indan-1-one of the formula 2 which has identical characteristic of product obtained for the Example 1, step-2.

Step-3

Process for the Preparation of 7-[4-[4-(2,3-dichlorophenyl)-1-piperazinyl]butoxy]-3, dihydro-1(H)-quinoline-2-one(Aripiprazole)

The 6-[4-[4-(2,3-dichlorophenyl)-1-piperazinyl]butoxy]-indan-1-one prepared by the step (2) (15 gm, 34.63 mmol) and 90 ml of trifluoroacetic acid was added and sodium azide (9 gm, 138.46 mmol) was added in portion wise at 65° C. The reaction mixture was maintained at 65° C. for 8-10 hrs. After the maintenance period was over the reaction mixture was quenched into 100 gm crushed ice, extracted with chloroform, and the chloroform basified with aqueous ammonia solution and separated the organic layer. The organic layer was dried with anhydrous sodium sulphate and concentrated under reduced pressure to get a residue 19 g, Which on crystallisation with methanol/toluene and acetone to give pure Aripiprazole of the formula A.

ADVANTAGES OF THE INVENTION

1. The Aripiprazole prepared is of high purity—greater than 99%
2. Avoids the formation of problematic unremovable impurity.
2. Provides novel intermediates of the formulae 2 and 3.

The invention claimed is:
1. A process for the preparation of aripiprazole of formula (1),

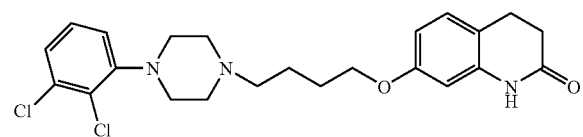

comprising:
(i) reacting a compound of formula (11)

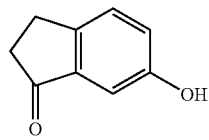

with 1,4-dihalobutane of formula (12)

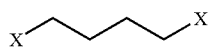

in the presence of a suitable base and solvent at a temperature in the range of 80° C. to 120° C. to form a compound of formula (3)

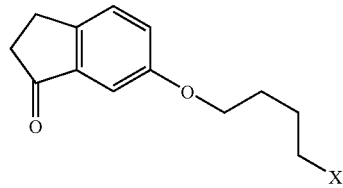

wherein X in formula (3) represents Cl or Br;
(ii) reacting the compound of formula (3) obtained in step (i) with compound of formula (9)

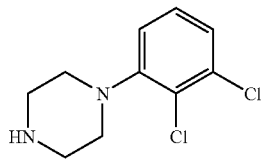

in the presence of a suitable base, phase transfer catalyst and solvent at a temperature in the range of 90° C. to 110° C. to form a compound of formula (2)

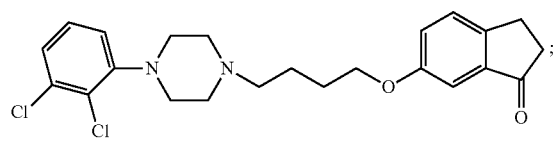

(iii) reacting the resulting compound of formula (2) obtained in step (ii) with an azide reagent in the presence of acid at a temperature in the range of 50° C. to 70° C. to obtain the compound of formula (1); and optionally
(iv) recrystallizing the compound of formula (1).

2. The process of claim 1 wherein the base used in step (i) is selected from the group consisting of sodium hydride, sodium methoxide, triethylamine, potassium carbonate, sodium bicarbonate, and sodium carbonate.

3. The process of claim 1 wherein the solvent used in step (i) is selected from the group consisting of acetone, chloroform, methylene chloride, ethylene dichloride, dimethyl formamide, dimethylsuphoxide, acetonitrile, and 1,4-dihalobutane.

4. The process of claim 1 wherein the temperature used in step (i) is between 100° C. and 110° C.

5. The process of claim 1 wherein the base used in step (ii) is selected from the group consisting of sodium carbonate, potassium carbonate, sodium bicarbonate, potassium bicarbonate, sodium hydride, potassium hydride, and triethylamine.

6. The process of claim 1 wherein the solvent used in step (ii) is selected from the group consisting of acetonitrile, acetone, dimethyl formamide, dimethyl suffoxide, ethanol, methanol, n-Butanol, and water.

7. The process of claim 1 wherein the temperature used in step (ii) is between 90° C. and 110° C.

8. The process of claim 1 wherein the phase transfer catalyst used in step (ii) is selected from the group consisting of tetra butylammonium chloride, tetra butylammonium bromide, benzyl triethyl ammonium chloride and phenyltrimethyl ammonium chloride.

9. The process of claim 1 wherein the acid used in step (iii) is selected from the group consisting of sulfuric acid, aluminum chloride, boron trifluoro etherate, trifluoro acetic acid, methane sulfonic acid, chloroacetic acid, dichloroacetic acid and trifluoro methane sulfonic acid.

10. The process of claim 1 wherein the azide reagent used in step (iii) is selected from the group consisting of trimethylsilylazide and sodium azide.

11. The process of claim 1 wherein the temperature used in step (iii) is between 50° C. and 70° C.

12. The process of claim 1 wherein the azide reagent used in step (iii) is sodium azide and wherein the amount of sodium azide used in step (iii) is 1-5 moles equivalent with respect to the compound of formula (2) used

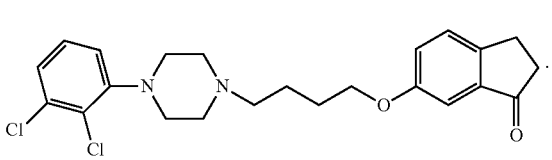

13. The process of claim 1 wherein the solvent used for recrystallization in step (iii) is selected from the group consisting of acetone, chloroform, methylene chloride, ethylene dichloride, dimethyl formamide, dimethylsulphoxide, acetonitrile, and methanol.

* * * * *